United States Patent
Shimizu (10) Patent No.: US 11,302,004 B2
(45) Date of Patent: Apr. 12, 2022

(54) CONTROL APPARATUS, RADIOGRAPHIC IMAGING SYSTEM, CONTROL METHOD, AND STORAGE MEDIUM

(71) Applicant: CANON KABUSHIKI KAISHA, Tokyo (JP)

(72) Inventor: Yasutomo Shimizu, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 200 days.

(21) Appl. No.: 16/255,201

(22) Filed: Jan. 23, 2019

(65) Prior Publication Data

US 2019/0236781 A1 Aug. 1, 2019

(30) Foreign Application Priority Data

Jan. 30, 2018 (JP) .............................. JP2018-013688

(51) Int. Cl.
G06K 9/00 (2006.01)
G06T 7/00 (2017.01)
G16H 30/40 (2018.01)

(52) U.S. Cl.
CPC .......... *G06T 7/0014* (2013.01); *G16H 30/40* (2018.01); *G06T 2207/10116* (2013.01); *G06T 2207/20016* (2013.01)

(58) Field of Classification Search
CPC ......... G06T 7/0014; G06T 2207/20016; G06T 2207/30168; G06T 7/0012; G06T 2207/10116; G16H 30/40; A61B 6/464; A61B 6/5211; A61B 6/54

USPC ......................................................... 382/132
See application file for complete search history.

(56) References Cited

U.S. PATENT DOCUMENTS

| 5,757,952 A * | 5/1998 | Buytaert ................... G06T 3/40 382/132 |
| 6,480,619 B1 * | 11/2002 | Vuylsteke ............. G06T 3/4007 382/132 |
| 2009/0189900 A1 * | 7/2009 | Furukawa ............ H04N 1/3935 345/428 |
| 2015/0193948 A1 * | 7/2015 | Kawamura .......... A61B 6/5264 382/132 |
| 2015/0327828 A1 * | 11/2015 | Kawamura ............. G06F 19/00 345/632 |

FOREIGN PATENT DOCUMENTS

| JP | 2006-376 A | 1/2006 |
| JP | 2006000376 | * 1/2006 |
| JP | 2014000134 A | 1/2014 |

* cited by examiner

*Primary Examiner* — Van D Huynh
(74) *Attorney, Agent, or Firm* — Canon U.S.A., Inc. IP Division (57) ABSTRACT

A control apparatus includes a reception unit that receives a plurality of reduced images included in a radiographic image in stages from a radiographic imaging apparatus, and a display control unit that, in a case where the radiographic image meets a pre-determined standard, displays a first image generated from the reduced images on a display unit, and in a case where the radiographic image does not meet the pre-determined standard, displays on the display unit a second image generated from more reduced images than the reduced images from which the first image is generated.

19 Claims, 7 Drawing Sheets

CONTROL APPARATUS, RADIOGRAPHIC IMAGING SYSTEM, CONTROL METHOD, AND STORAGE MEDIUM

BACKGROUND

Field

The present disclosure relates to a control apparatus, a radiographic imaging system, a control method, and a storage medium.

Description of the Related Art

Conventionally, as a medical image capturing system in the medical field, a radiographic imaging system using radiation is known. Owing to the digitalization of a radiographic imaging system, the system in which a radiographic imaging apparatus generates a digital radiographic captured image, thereby enabling checking of an image immediately after radiographic imaging is widely used. This improves a workflow as compared with a conventional imaging method using a film and enables imaging in a short cycle. There is also known a system in which radiographic captured images are received in stages from a radiographic imaging apparatus, an intermediate image is generated by reducing data based on the received radiographic captured images, and the intermediate image is displayed, thereby shortening the time until an image is displayed.

Japanese Patent Application Laid-Open No. 2006-376 discusses a technique for detecting an image that does not meet a standard for a diagnosis medical image and is likely to require re-imaging, as an image likely to require re-imaging, and giving warning in a case where such an image is detected. Based on this, an operator determines whether re-imaging is necessary. However, in order for the operator to determine whether re-imaging is necessary, ultimately, the operator needs to perform visual confirmation work. Thus, various improvements are desired.

SUMMARY

The present disclosure is directed to improving the efficiency of confirmation work for determining whether re-imaging is necessary. According to an aspect of the present disclosure, a control apparatus includes a reception unit configured to receive a plurality of reduced images included in a radiographic image in stages from a radiographic imaging apparatus, and a display control unit configured to, in a case where the radiographic image meets a pre-determined standard, display a first image generated from the reduced images on a display unit, and in a case where the radiographic image does not meet the pre-determined standard, display on the display unit a second image generated from more reduced images than the reduced images from which the first image is generated.

Further features will become apparent from the following description of exemplary embodiments with reference to the attached drawings.

DESCRIPTION OF THE EMBODIMENTS

Exemplary embodiments will be described below with reference to the drawings.

Figure 1:
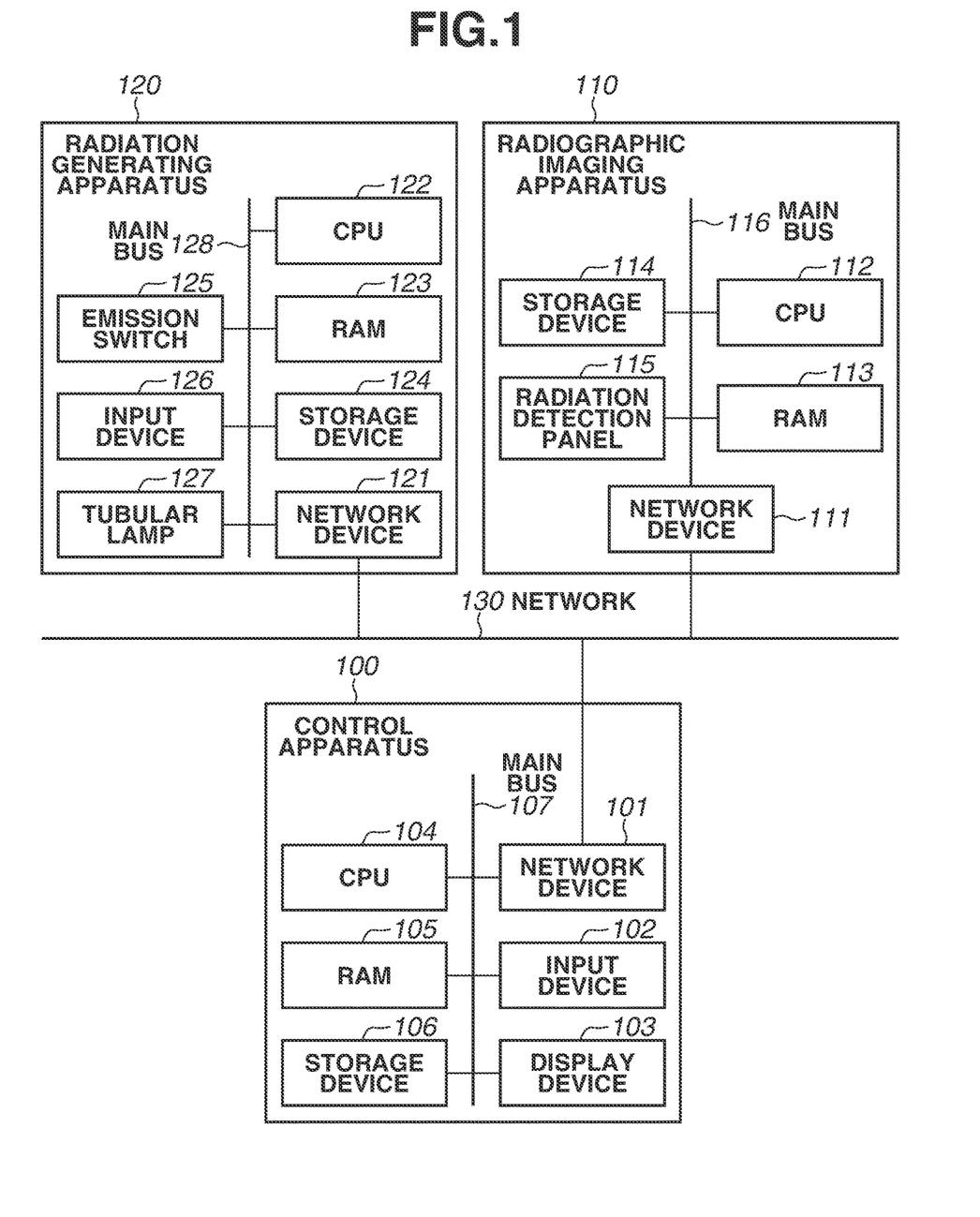
FIG. 1 is a hardware configuration diagram of a radiographic imaging system.

A first exemplary embodiment will be described. FIG. 1 is a hardware configuration diagram of a radiographic imaging system. This system includes a control apparatus 100, a radiographic imaging apparatus 110, and a radiation generating apparatus 120 connected via the network 130. The network 130 may be a wired network or a wireless network.

The control apparatus 100 is an apparatus that includes an information processing apparatus such as a computer and communicates with the radiographic imaging apparatus 110 and controls radiographic imaging. The control apparatus 100 communicates with the radiation generating apparatus 120 and acquires information regarding emission of radiation from the radiation generating apparatus 120. The control apparatus 100 includes a network device 101 that connects to the network 130, an input device 102 such as a keyboard that receives a user operation, and a display device 103 such as a liquid crystal display that displays an operation screen and a radiographic image. The control apparatus 100 includes a central processing unit (CPU) 104 that controls the entire apparatus, a random-access memory (RAM) 105 that provides a work space for the CPU 104, and a storage device 106 that stores various control programs and a radiographic image received from the radiographic imaging apparatus 110. The devices included in the control apparatus 100 are connected by a main bus 107 and can transmit and receive data to and from each other. While the input device 102 and the display device 103 are separate devices in the above description, an operation unit in which these devices are integrated can be used.

The radiographic imaging apparatus 110 is an apparatus that, based on an instruction from the control apparatus 100, transitions to a state where the radiographic imaging apparatus 110 can perform imaging, performs radiographic imaging in synchronization with the radiation generating apparatus 120, and generates an image based on radiation emitted from the radiation generating apparatus 120. The radiographic imaging apparatus 110 includes a network device 111 that connects to the network 130, a CPU 112 that controls the entire apparatus, a RAM 113 that provides a work space for the CPU 112, and a storage device 114 that stores control programs and a generated image. Further, the radiographic imaging apparatus 110 includes a radiation detection panel 115. The radiation detection panel 115 includes, for example, a flat panel detector (FPD) and generates an electric signal based on the amount of radiation, thereby generating a radiographic image. The devices included in the radiographic imaging apparatus 110 are connected by a main bus 116 and can transmit and receive data to and from each other. The number of radiographic imaging apparatuses 110 is not limited to one, and the configuration can be such that a plurality of radiographic imaging apparatuses are used.

The radiographic imaging apparatus 110 reduces pixels at a predetermined reducing rate from a radiographic image obtained by radiographic imaging and generates a plurality of reduced images divided into equal numbers of pixels at predetermined pixel intervals. In this case, the plurality of reduced images are included in the radiographic image. The radiographic imaging apparatus 110 transmits the plurality of reduced images in stages to the control apparatus 100.

The radiation generating apparatus 120 is an apparatus that detects a radiation emission instruction from an emission switch 125, and based on an emission condition set using an input device 126 such as an operation panel for receiving a user operation, causes a tubular lamp 127 to generate radiation. The radiation generating apparatus 120 includes a network device 121 that connects to the network 130, a CPU 122 that controls the entire apparatus, a RAM 123 that provides a work space for the CPU 122, and a storage device 124 that stores control programs. The devices included in the radiation generating apparatus 120 are connected by a main bus 128 and can transmit and receive data to and from each other.

The function and the processing of the control apparatus 100 described below are achieved by the CPU 104 reading a program stored in the storage device 106 and executing the program. Similarly, the function and the processing of the radiographic imaging apparatus 110 are achieved by the CPU 112 reading a program stored in the storage device 114 and executing the program. The function and the processing of the radiation generating apparatus 120 are achieved by the CPU 122 reading a program stored in the storage device 124 and executing the program.

Figure 2:
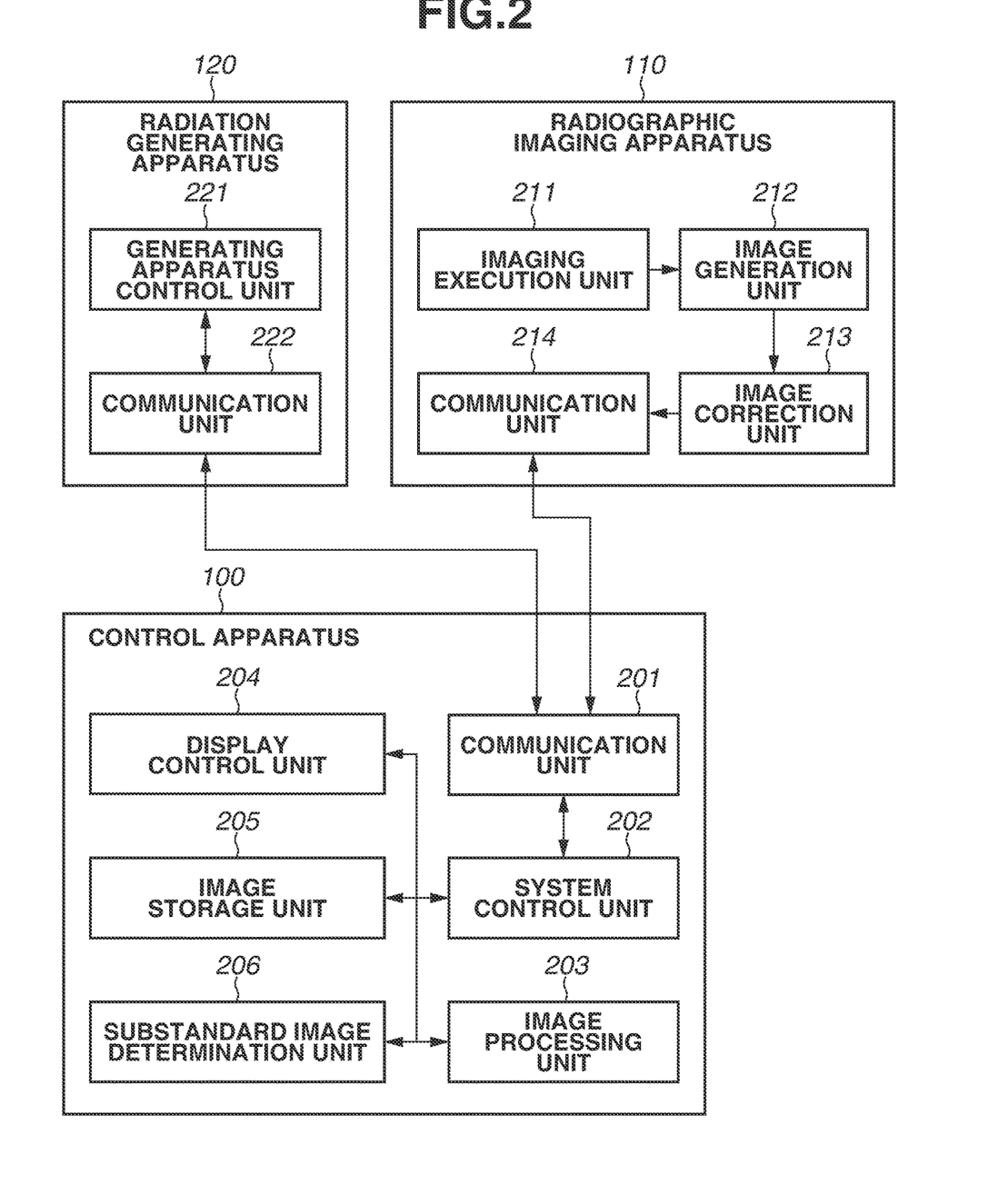
FIG. 2 is a functional configuration diagram of the radiographic imaging system.

FIG. 2 is a functional configuration diagram of the radiographic imaging system. The control apparatus 100 includes a communication unit 201, a system control unit 202, an image processing unit 203, a display control unit 204, an image storage unit 205, and a substandard image determination unit 206. The communication unit 201 controls the network device 101 to perform communication. The system control unit 202 acquires emission information of the radiation generating apparatus 120 and imaging information of the radiographic imaging apparatus 110 and manages the states of the radiation generating apparatus 120 and the radiographic imaging apparatus 110 via the communication unit 201. The system control unit 202 acquires a plurality of reduced images included in a radiographic image in stages from the radiographic imaging apparatus 110 via the communication unit 201. The system control unit 202 executes the basic function of the radiographic imaging apparatus 110 and controls the operations of the units of the radiographic imaging apparatus 110.

The image processing unit 203 generates a high-definition image from the reduced images included in the radiographic image acquired via the system control unit 202. The image processing unit 203 generates a display high-definition image, an intermediate image, and a display intermediate image. The high-definition image is an image generated based on all the reduced images acquired in stages from the radiographic imaging apparatus 110, i.e., all the reduced images included in the radiographic image. In contrast, the intermediate image is an image generated based on a smaller number of reduced images than the number of all the reduced images included in the radiographic image. The number of reduced images used to generate the intermediate image is pre-determined. As described above, the intermediate image is an image having lower image quality than the high-definition image. The display high-definition image is an image obtained by performing an enlargement or reduction process on the high-definition image for display on the display device 103. The display intermediate image is an image obtained by performing an enlargement or reduction process on the intermediate image for display on the display device 103.

In the present exemplary embodiment, an image generated based on all the reduced images included in the radiographic image is considered as the high-definition image. However, the high-definition image may only need to be an image generated based on a greater number of reduced images than the number of reduced images used to generate the intermediate image. The intermediate image and the high-definition image are examples of a first image and a second image, respectively.

The display control unit 204 performs control to display various types of information on the display device 103. The display control unit 204 performs control to, for example, display an image generated by the image processing unit 203. The display control unit 204 reflects processing on an image based on an instruction from the system control unit 202 based on an operation on the input device 102 or displays the determination result of the substandard image determination unit 206. The image storage unit 205 saves the high-definition image generated by the image processing unit 203, and emission information of the radiation generating apparatus 120 and imaging information of the radiographic imaging apparatus 110 related to the high-definition image. The substandard image determination unit 206 determines whether an image obtained by irradiation of radiation is a substandard image. The substandard image is a radiographic image that does not meet a standard for a diagnosis medical image and is likely to require re-imaging. Based on a pre-determined condition, the substandard image determination unit 206 determines whether the image is a substandard image. In the present exemplary embodiment, the substandard image determination unit 206 determines as a substandard image an image in which a body movement is detected. As another example, the substandard image determination unit 206 can determine as a substandard image an image in which a particular part is missing or an image in which the amount of emitted radiation exceeds a pre-set threshold.

The radiographic imaging apparatus 110 includes an imaging execution unit 211, an image generation unit 212, an image correction unit 213, and a communication unit 214. The imaging execution unit 211 acquires a radiographic image obtained by emitting radiation. The imaging execution unit 211 acquires a dark image (a dark output) when radiation is not emitted. Based on the radiographic image generated by the imaging execution unit 211, the image generation unit 212 generates imaging information with a small data size. In the present exemplary embodiment, as the imaging information, the average value of the pixel values of the radiographic image is used. The image correction unit 213 corrects the radiographic image using the dark image and generates a processed radiographic image as a corrected image. The communication unit 214 controls the network device 111 to perform communication. For example, the communication unit 214 transmits the imaging information generated by the image generation unit 212 to the control apparatus 100. The communication unit 214 transmits a plurality of reduced images included in the radiographic image generated by the image correction unit 213 in stages to the control apparatus 100.

The radiation generating apparatus 120 includes a generating apparatus control unit 221 and a communication unit 222. The generating apparatus control unit 221 detects a radiation emission instruction from the emission switch 125, and based on a setting made using the input device 126, controls the tubular lamp 127 to generate radiation. The communication unit 222 controls the network device 111 to perform communication. For example, when the generating apparatus control unit 221 detects a radiation emission instruction from the emission switch 125, the communication unit 222 transmits an emission start notification to the radiographic imaging apparatus 110. Then, after receiving an emission permission notification from the radiographic imaging apparatus 110, the generating apparatus control unit 221 performs control to generate radiation and performs synchronous communication. The generating apparatus control unit 221 transmits emission information of the radiation generating apparatus 120 to the radiographic imaging apparatus 110.

Figure 3:
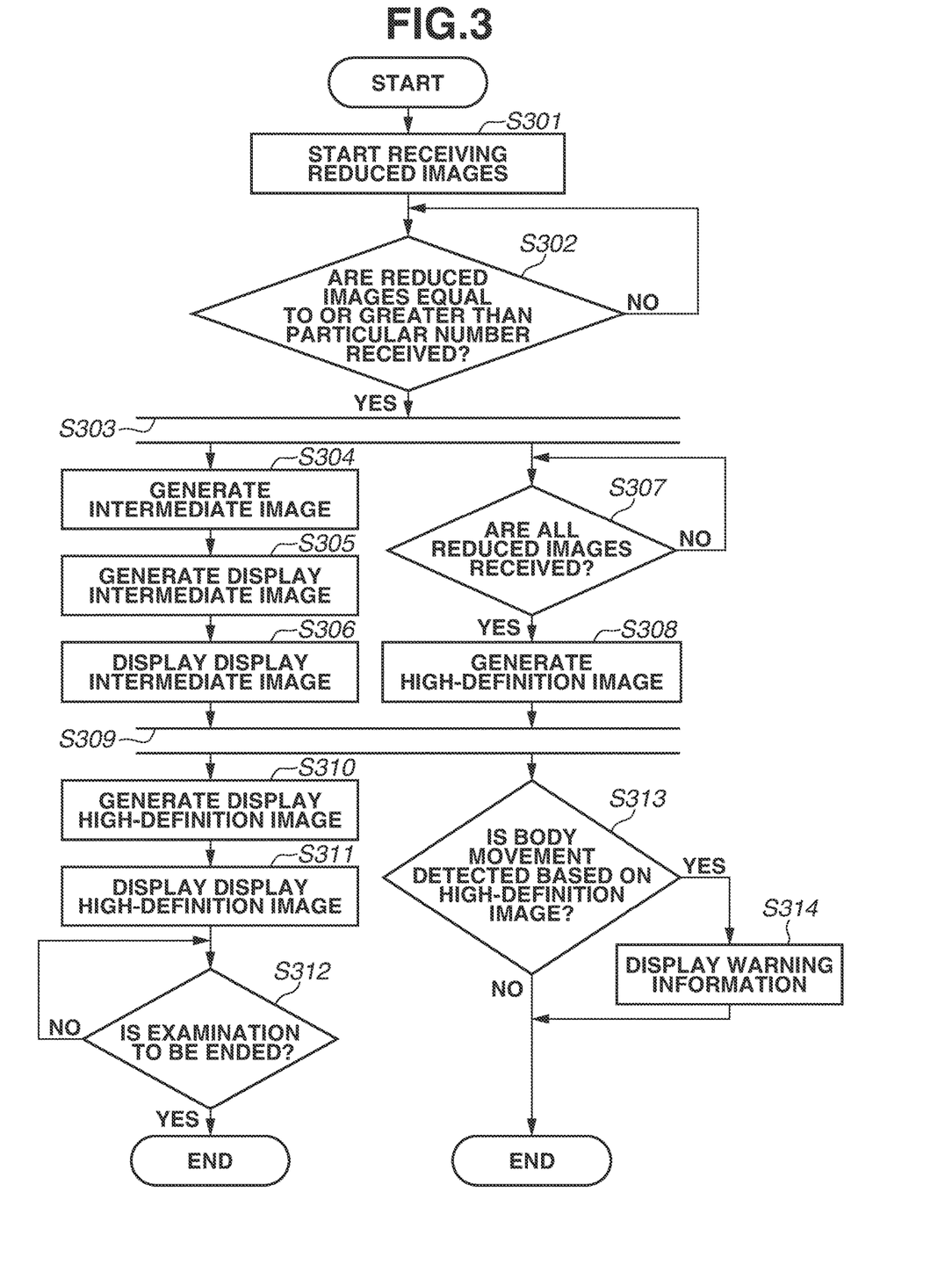
FIG. 3 is a flowchart illustrating a display process for displaying a radiographic image in an image quality-priority mode.
Figure 4:
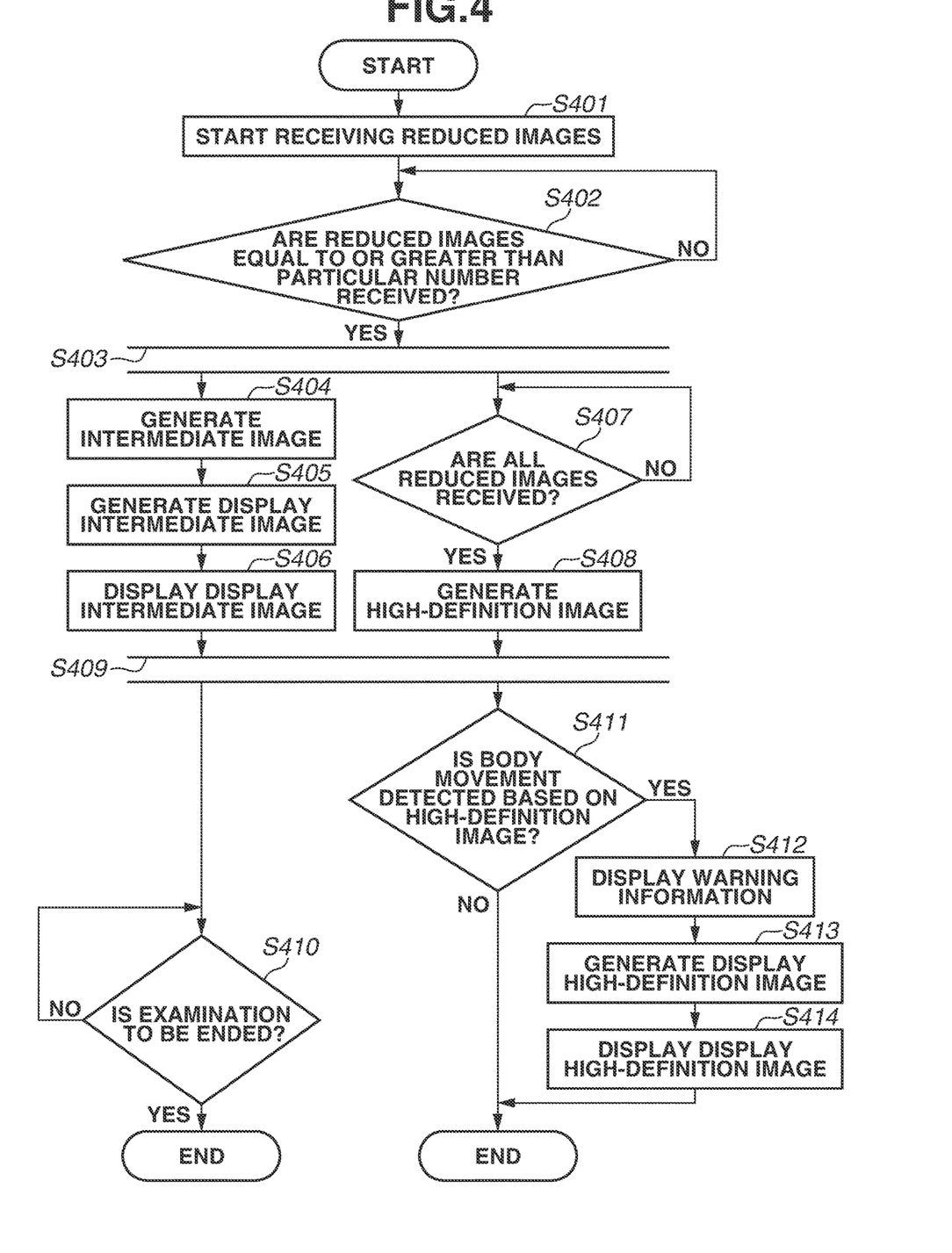
FIG. 4 is a flowchart illustrating a display process for displaying a radiographic image in a speed-priority mode.

Next, a description will be provided of a process in which the control apparatus 100 displays a radiographic image acquired from the radiographic imaging apparatus 110. Regarding a display process for displaying a radiographic image, the control apparatus 100 has two modes, an image quality-priority mode and a speed-priority mode. The image quality-priority mode is an operation mode that prioritizes the image quality of the radiographic image over the display speed of the radiographic image. The speed-priority mode is an operation mode that prioritizes the display speed of the radiographic image over the image quality of the radiographic image. According to a user operation, the system control unit 202 sets either the image quality-priority mode or the speed-priority mode. FIG. 3 is a flowchart illustrating a display process for displaying a radiographic image in the image quality-priority mode. FIG. 4 is a flowchart illustrating a display process for displaying a radiographic image in the speed-priority mode.

In the image quality-priority mode, in step S301, the system control unit 202 starts receiving, in stages from the radiographic imaging apparatus 110, a plurality of reduced images included in a radiographic captured image generated by the image correction unit 213 of the radiographic imaging apparatus 110. Next, in step S302, the system control unit 202 determines whether the number of the received reduced images is greater than or equal to a pre-determined particular number. The system control unit 202 continues to receive reduced images until the number of the received reduced images is greater than or equal to the particular number (NO in step S302). If the number of the received reduced images is greater than or equal to the particular number (YES in step S302), the processing proceeds to step S303. The particular number is, for example, half the number of all the reduced images.

In step S303, the system control unit 202 performs control to start parallel processing between the processes of step S304 and subsequent steps and the processes of step S307 and subsequent steps. In step S304, based on the particular number of received reduced images, the image processing unit 203 generates an intermediate image. Next, in step S305, based on the particular number of received reduced images, the image processing unit 203 generates a display intermediate image. Next, in step S306, the display control unit 204 performs control to display the display intermediate image on the display device 103.

In step S307, the system control unit 202 determines whether the reception of all the reduced images from the radiographic imaging apparatus 110 is completed. The system control unit 202 waits until all the reduced images are received (NO in step S307). If all the reduced images are received (YES in step S307), the processing proceeds to step S308. In step S308, based on all the reduced images received from the radiographic imaging apparatus 110, the system control unit 202 generates a high-definition image. Then, the image processing unit 203 saves the high-definition image in the storage device 106. If the process of step S306 is completed, and the process of step S308 is completed, the processing proceeds to step S309.

In step S309 the system control unit 202 performs control to start parallel processing between the processes of step S310 and subsequent steps and the processes of step S313 and subsequent steps. In step S310, based on all the reduced images received from the radiographic imaging apparatus 110, the image processing unit 203 generates a display high-definition image. Next, in step S311, the display control unit 204 performs control to display the display high-definition image on the display device 103. That is, by the process of step S311, the display on the display device 103 switches from the display intermediate image displayed in step S306 to the display high-definition image. At this time, if receiving a user operation, the system control unit 202 performs a process based on the user operation. Examples of the process include the enlargement or reduction of the image, a gradation process, and an input process for inputting examination information. Next, in step S312, the system control unit 202 determines whether an examination end instruction is received based on a user operation. The system control unit 202 waits until an examination end instruction is received (NO in step S312). If an examination end instruction is received (YES in step S312), the processing ends.

In step S313, based on the high-definition image, the substandard image determination unit 206 determines whether the received radiographic image is a substandard image, i.e., whether a body movement is detected. If a body movement is detected (YES in step S313), the processing proceeds to step S314. If a body movement is not detected (NO in step S313), the processing ends. In step S314, the display control unit 204 performs control to display, on the display device 103, warning information indicating that a body movement is detected. The display control unit 204 performs control to display a frame line indicating an area where the body movement is detected, in a superimposed manner on the radiographic image that is being displayed. Then, the processing ends. When the processing ends, the display control unit 204 performs control to end radiographic imaging and performs the process of transferring the high-definition image to external storage (not illustrated).

Next, with reference to FIG. 4, a description is provided of the display process for displaying a radiographic image in the speed-priority mode. The processes of steps S401 to S408 illustrated in FIG. 4 are similar to the processes of steps S301 to S308 illustrated in FIG. 3. In step S409, the system control unit 202 performs control to start parallel processing between the processes of step S410 and subsequent steps and the processes of step S411 and subsequent steps. In step S410, the system control unit 202 determines whether an examination end instruction is received. The system control unit 202 waits until an examination end instruction is received (NO in step S410). If an examination end instruction is received (YES in step S410), the processing ends. This process is similar to the process of step S312. In the speed-priority mode, when the process of step S406 is completed, the system control unit 202 can receive a user operation. If receiving a user operation, the system control unit 202 can perform a process based on the user operation.

In step S411, based on the high-definition image, the substandard image determination unit 206 determines whether the received radiographic image is a substandard image, i.e., whether a body movement is detected. If a body movement is detected (YES in step S411), the processing proceeds to step S412. If a body movement is not detected (NO in step S411), the processing ends.

In step S412, the display control unit 204 performs control to display, on the display device 103, warning information indicating that a body movement is detected. The display control unit 204 performs control to display a frame line indicating an area where the body movement is detected, in a superimposed manner on the radiographic image that is being displayed. This process is similar to the process of step S314. Next, in step S413, based on all the reduced images received from the radiographic imaging apparatus 110, the image processing unit 203 generates a display high-definition image. Next, in step S414, the display control unit 204 performs control to display the display high-definition image on the display device 103. That is, by the process of step S414, the display on the display device 103 switches from the display intermediate image displayed in step S406 to the display high-definition image. Then, the processing ends. The processing order of the processes of steps S412 and S413 is not particularly limited. Alternatively, step S412 can be performed after the processes of steps S413 and S414. In addition, the processes of steps S412 and S413 can be performed simultaneously.

As described above, in the speed-priority mode, when a display intermediate image is displayed on the display device 103, a user operation can be received. This can shorten the time from the confirmation of an imaging result by an operator to the end of an examination. If a body movement is detected, a display target is switched from the display intermediate image to a display high-definition image. In this way, the operator can determine whether to perform re-imaging by confirming the display high-definition image. This can prevent the operator from erroneously determining whether to perform re-imaging by confirming a low-resolution image. That is, it is possible to more accurately determine whether to perform re-imaging. If, a body movement is not detected, a display high-definition image is not displayed.

The radiographic imaging system (the control apparatus 100) according to the present disclosure includes a system control unit 202 that receives a plurality of reduced images included in a radiographic image in stages from a radiographic imaging apparatus 110, and a display control unit 204 that, in a case where the radiographic image meets a pre-determined standard, displays a first image generated from the reduced images on a display device 103, and in a case where the radiographic image does not meet the standard, displays on the display device 103 a second image generated from more reduced images than the reduced images from which the first image is generated. The second image is an image generated from all the reduced images included in the radiographic image. The first image is an image generated based on a smaller number of reduced images than all the reduced images included in the radiographic image.

In other words, the radiographic imaging system (the control apparatus 100) according to the present disclosure includes a system control unit 202 that receives a radiographic image from a radiographic imaging apparatus 110, and a display control unit 204 that, in a case where the radiographic image meets a pre-determined standard, displays a low-resolution image (a low-definition image) on a display device 103, and in a case where the radiographic image does not meet the standard, displays a high-resolution image (a high-definition image) on the display device 103.

The radiographic imaging system (the control apparatus 100) according to the present embodiment includes an image processing unit 203 that, in a case where the system control unit 202 receives a first number of the reduced images, generates the first image based on the first number of the reduced images, and in a case where the system control unit 202 receives a second number of the reduced images greater than the first number, generates the second image based on the second number of the reduced images. The radiographic imaging system (the control apparatus 100) according to the present embodiment includes a substandard image determination unit 206 that determines whether the radiographic image meets the standard based on the second image. Based on the first image, the substandard image determination unit 206 determines whether the radiographic image meets the standard.

The display control unit 204 performs control to, in a case where a resolution of the display device 103 is greater than or equal to a threshold and in a case where the radiographic image does not meet the standard, display the second image. The display control unit 204 performs control to, in a case where the resolution of the display device 103 is less than the threshold, display the first image, regardless of whether the radiographic image meets the standard.

The display control unit 204 performs control to, in a case where the radiographic image does not meet the standard, display, on the display device 103, information indicating that the radiographic image does not meet the standard. The display control unit 204 performs control to, in a case where the radiographic image does not meet the standard, display the second image such that an area of the second image where the radiographic image is determined as not meeting the standard is located in a center area of the display device 103.

Thus, it is possible to shorten the processing time as compared to a case where a display high-definition image is always displayed. As described above, the radiographic imaging apparatus 110 according to the present exemplary embodiment displays a display high-definition image if it is determined that a radiographic image is a substandard image. Thus, it is possible to improve the operability of confirmation work for determining whether re-imaging is necessary.

In the present exemplary embodiment, a display high-definition image and a display intermediate image are display targets. As a first variation, a high-definition image and an intermediate image can be display targets as other examples.

As a second variation, when displaying the display high-definition image in step S414, the display control unit 204 can display the display high-definition image by moving the display high-definition image so that the area where the body movement is detected is located in a center area of the display device 103. Similarly, also in step S314, the display control unit 204 can display the display high-definition image by moving the display high-definition image so that the area where the body movement is detected is located in the center area of the display device 103. This makes it easy for the operator to confirm an area that is determined as not satisfying a condition.

Figure 5:
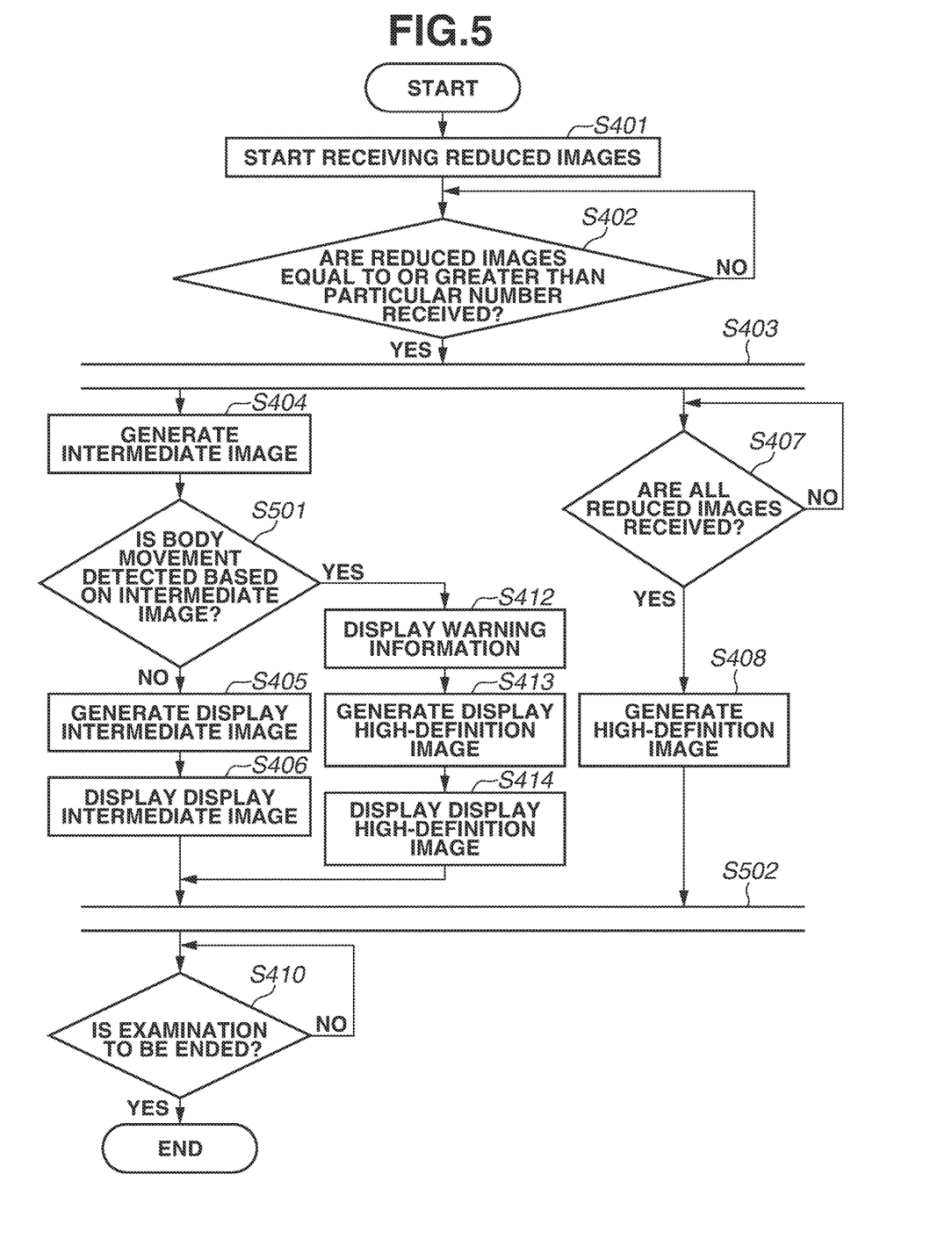
FIG. 5 is a flowchart illustrating a display process according to a second exemplary embodiment.

Next, a radiographic imaging system according to a second exemplary embodiment will be described focusing mainly on the differences from the radiographic imaging system according to the first exemplary embodiment. In the radiographic imaging system according to the second exemplary embodiment, in the speed-priority mode, based on an intermediate image, the control apparatus 100 determines whether a radiographic image is a substandard image (determines the presence or absence of a body movement). Consequently, a body movement can be detected before a high-definition image is generated. Thus, it is possible to shorten the time until the display high-definition image is displayed.

FIG. 5 is a flowchart illustrating a display process for displaying a radiographic image in the speed-priority mode by the control apparatus 100 according to the second exemplary embodiment. Among processes in the display process illustrated in FIG. 5, processes similar to the processes in the display process according to the first exemplary embodiment described with reference to FIG. 4 are designated by the same numbers. After the process of step S404, the processing proceeds to step S501.

In step S501, based on the intermediate image, the substandard image determination unit 206 determines whether the received radiographic image is a substandard image, i.e., whether a body movement is detected. If a body movement is not detected (NO in step S501), the processing proceeds to step S405. That is, in this case, a display intermediate image is displayed on the display device 103. If a body movement is detected (YES in step S501), the processing proceeds to step S412. That is, in this case, on the display device 103, warning information is displayed, and a display high-definition image is displayed.

After the processes of steps S406 and S414, the processing proceeds to step S502. In step S502, if either the process of step S406 or step S414 ends, and the process of step S408 ends, the processing proceeds to step S410. The rest of the configuration and the processing of the radiographic imaging system according to the present exemplary embodiment is similar to the configuration and the processing of the radiographic imaging system according to the first exemplary embodiment.

As described above, based on an intermediate image, the control apparatus 100 according to the second exemplary embodiment determines whether a radiographic image is a substandard image. If the radiographic image is determined as a substandard image, the control apparatus 100 according to the second exemplary embodiment generates a display high-definition image. Consequently, also in the radiographic imaging system according to the second exemplary embodiment, it is possible to improve the operability of confirmation work for determining whether re-imaging is necessary.

Figure 6:
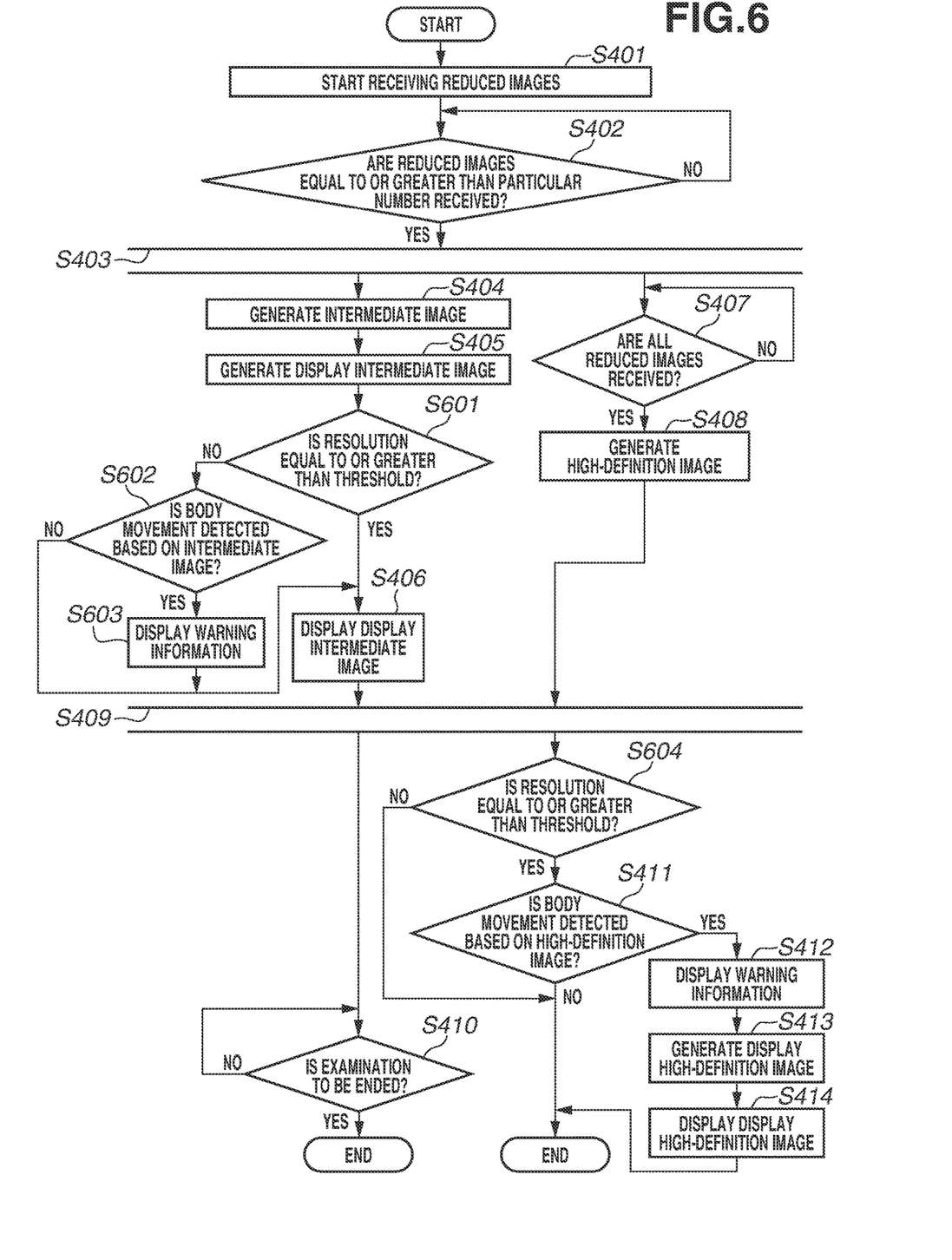
FIG. 6 is a flowchart illustrating a display process according to a third exemplary embodiment.

Next, a radiographic imaging system according to a third exemplary embodiment will be described focusing mainly on the differences from the radiographic imaging systems according to other exemplary embodiments. In the radiographic imaging system according to the third exemplary embodiment, the radiographic imaging apparatus 110 controls switching to a display high-definition image based on the resolution of the display device 103. There is a case where, depending on the monitor size or the resolution of the display device 103, the display of a display high-definition image is not useful in determining whether to perform re-imaging. The control apparatus 100 according to the present exemplary embodiment performs control not to switch to a display high-definition image in such a case.

FIG. 6 is a flowchart illustrating a display process for displaying a radiographic image in the speed-priority mode by the control apparatus 100 according to the third exemplary embodiment. Among processes in the display process illustrated in FIG. 6, processes similar to the processes in the display process according to the first exemplary embodiment described with reference to FIG. 4 are designated by the same numbers. After the process of step S405, the processing proceeds to step S601. In step S601, the system control unit 202 determines whether the resolution of a screen of the display device 103 is greater than or equal to a threshold. In this case, the threshold is pre-set. For example, a resolution of 1024×1280 is set as the threshold. The threshold only need to be resolution enabling distinction between a display intermediate image and a display high-definition image in visual determination, and is not limited to that in the exemplary embodiment. If the resolution is greater than or equal to the threshold (YES in step S601), the processing proceeds to step S406. If the resolution is less than the threshold (NO in step S601), the processing proceeds to step S602.

In step S602, based on the intermediate image, the substandard image determination unit 206 determines whether the received radiographic image is a substandard image, i.e., whether a body movement is detected. If a body movement is not detected (NO in step S602), the processing proceeds to step S406. If a body movement is detected (YES in step S602), the processing proceeds to step S603. In step S603, the display control unit 204 performs control to display, on the display device 103, warning information indicating that a body movement is detected. The display control unit 204 performs control to display, in a superimposed manner on the radiographic image that is being displayed, a frame line indicating an area where the body movement is detected. This process is similar to the process of step S412.

In step S409, the system control unit 202 performs control to start parallel processing between the processes of step S410 and subsequent steps and the processes of step S604 and subsequent steps. In step S604, the system control unit 202 determines whether the resolution of the display device 103 is greater than or equal to a threshold. If the resolution is greater than or equal to the threshold (YES in step S604), the processing proceeds to step S411. If the resolution is less than the threshold (NO in step S604), the processing ends. As described above, if the resolution is greater than or equal to the threshold and a body movement is detected, the radiographic imaging apparatus 110 performs control to display a display high-definition image. If the resolution is less than the threshold, the radiographic imaging apparatus 110 performs control not to switch a display target to a display high-definition image, regardless of the presence or absence of a body movement. The rest of the configuration and the processing of the radiographic imaging system according to the third exemplary embodiment is similar to the configuration and the processing of each of the radiographic imaging systems according to the other exemplary embodiments.

As described above, the control apparatus 100 according to the third exemplary embodiment restricts the display of a display high-definition image based on the resolution of the display device. Thus, it is possible to prevent a display high-definition image from being unnecessarily displayed.

Figure 7:
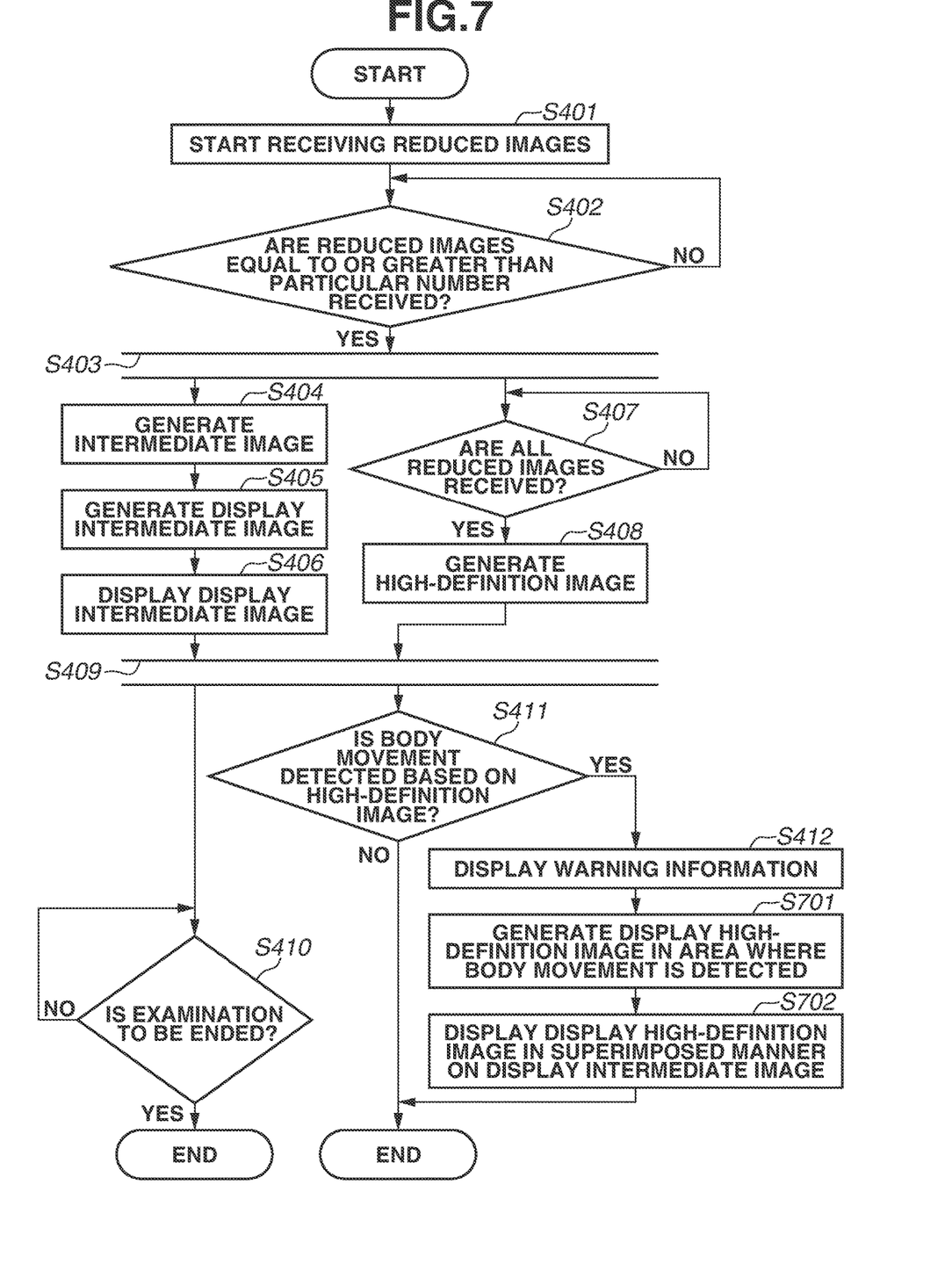
FIG. 7 is a flowchart illustrating a display process according to a fourth exemplary embodiment.

Next, a radiographic imaging system according to a fourth exemplary embodiment will be described focusing mainly on the differences from the radiographic imaging systems according to the other exemplary embodiments. In the radiographic imaging system according to the fourth exemplary embodiment, the control apparatus 100 generates and displays a display high-definition image only in an area where a radiographic image is determined as a substandard image.

FIG. 7 is a flowchart illustrating a display process for displaying a radiographic image in the speed-priority mode by the control apparatus 100 according to the fourth exemplary embodiment. Among processes in the display process illustrated in FIG. 7, processes similar to the processes in the display process according to the first exemplary embodiment described with reference to FIG. 4 are designated by the same numbers. After the process of step S412, the processing proceeds to step S701. In step S701, the image processing unit 203 generates a display high-definition image only in the area where the body movement is detected. Next, in step S702, the display control unit 204 displays the display high-definition image in a superimposed manner on the area where the body movement is detected in the display intermediate image. The processing then ends. The processing order of the processes of steps S412 and S701 is not particularly limited. The rest of the configuration and the processing of the radiographic imaging system according to the fourth exemplary embodiment is similar to the configuration and the processing of each of the radiographic imaging systems according to the other exemplary embodiments.

As described above, the control apparatus 100 according to the fourth exemplary embodiment displays a display high-definition image only in an area where a body movement is detected. Thus, it is possible to shorten the time until the display high-definition image is displayed.

While desirable exemplary embodiments of the present disclosure have been described in detail, these exemplary embodiments are not seen to be limiting, and can be modified and changed in various manners within the scope of the present disclosure described in the appended claims.

Other Exemplary Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-013688, filed Jan. 30, 2018, which is hereby incorporated by reference herein in its entirety.

What is claimed is:

1. A control apparatus comprising:
   a reception unit configured to receive a plurality of reduced images included in a radiographic image in stages from a radiographic imaging apparatus; and
   a display control unit configured to, in a case where the radiographic image meets a pre-determined standard, display a first image generated from reduced images included in the plurality of reduced images on a display unit, and in a case where the radiographic image does not meet the pre-determined standard, display on the display unit a second image generated from reduced images which are included in the plurality of reduced images and of which the number is larger than the number of the reduced images from which the first image is generated,
   wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

2. The control apparatus according to claim 1, further comprising a generation unit configured to, in a case where the reception unit receives a first number of the reduced images, generate the first image based on the first number of the reduced images, and in a case where the reception unit receives a second number of the reduced images greater than the first number, generate the second image based on the second number of the reduced images.

3. The control apparatus according to claim 1, further comprising a determination unit configured to, based on the second image, determine whether the radiographic image meets the pre-determined standard.

4. The control apparatus according to claim 1, further comprising a determination unit configured to, based on the first image, determine whether the radiographic image meets the pre-determined standard.

5. The control apparatus according to claim 1, further comprising:
   a first generation unit configured to, in a case where the reception unit receives a first number of the reduced images, generate the first image based on the first number of the reduced images;
   a determination unit configured to, based on the first image, determine whether the radiographic image meets the pre-determined standard; and
   a second generation unit configured to, in a case where the determination unit determines that the radiographic image does not meet the pre-determined standard, generate the second image based on a second number of the reduced images,
   wherein the display control unit performs control to, in a case where the determination unit determines that the radiographic image does not meet the pre-determined standard, display the second image.

6. The control apparatus according to claim 1, wherein the display control unit performs control to, in a case where a resolution of the display unit is greater than or equal to a threshold and the radiographic image does not meet the pre-determined standard, display the second image.

7. The control apparatus according to claim 6, wherein the display control unit performs control to, in a case where the resolution of the display unit is less than the threshold, display the first image, regardless of whether the radiographic image meets the pre-determined standard.

8. The control apparatus according to claim 1, further comprising:
a first generation unit configured to, in a case where the reception unit receives a first number of the reduced images, generate the first image based on the first number of the reduced images; and
a second generation unit configured to, in a case where it is determined that the radiographic image does not meet the pre-determined standard, generate, based on a second number of the reduced images, the second image in an area where the radiographic image is determined as not meeting the pre-determined standard,
wherein the display control unit performs control to, in a case where the radiographic image does not meet the pre-determined standard, display the second image generated by the second generation unit in a superimposed manner on the first image.

9. The control apparatus according to claim 1, wherein the display control unit performs control to, in a case where the radiographic image does not meet the pre-determined standard, display, on the display unit, information indicating that the radiographic image does not meet the pre-determined standard.

10. The control apparatus according to claim 1, wherein the display control unit performs control to, in a case where the radiographic image does not meet the pre-determined standard, display an area where the radiographic image is determined as not meeting the pre-determined standard in the second image, such that the area is located in a center area of the display unit.

11. The control apparatus according to claim 1, wherein the second image is an image generated from all the reduced images included in the radiographic image.

12. The control apparatus according to claim 1, wherein the first image is an image generated based on a smaller number of reduced images than all the reduced images included in the radiographic image.

13. A control apparatus comprising:
a reception unit configured to receive a radiographic image from a radiographic imaging apparatus; and
a display control unit configured to, in a case where the radiographic image meets a pre-determined standard, display a low-resolution image on a display unit, and in a case where the radiographic image does not meet the pre-determined standard, display a high-resolution image on the display unit,
wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

14. A radiographic imaging system comprising:
a reception unit configured to receive a plurality of reduced images included in a radiographic image in stages from a radiographic imaging apparatus;
a display unit configured to display the radiographic image; and
a display control unit configured to, in a case where the radiographic image meets a pre-determined standard, display a first image generated from reduced images included in the plurality of reduced images on the display unit, and in a case where the radiographic image does not meet the pre-determined standard, display on the display unit a second image generated from reduced images which are included in the plurality of reduced images and of which the number is larger than the number of the reduced images from which the first image is generated,
wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

15. A radiographic imaging system comprising:
a reception unit configured to receive a radiographic image from a radiographic imaging apparatus;
a display unit configured to display the radiographic image; and
a display control unit configured to, in a case where the radiographic image meets a pre-determined standard, display a low-resolution image on the display unit, and in a case where the radiographic image does not meet the pre-determined standard, display a high-resolution image on the display unit,
wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

16. A control method comprising:
receiving a plurality of reduced images included in a radiographic image in stages from a radiographic imaging apparatus; and
displaying, in a case where the radiographic image meets a pre-determined standard, a first image generated from reduced images included in the plurality of reduced images on a display unit, and displaying, in a case where the radiographic image does not meet the pre-determined standard, on the display unit a second image generated from reduced images which are included in the plurality of reduced images and of which the number is larger than the number of the reduced images from which the first image is generated, and
wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

17. A control method comprising:
receiving a radiographic image from a radiographic imaging apparatus; and
displaying, in a case where the radiographic image meets a pre-determined standard, a low-resolution image on a display unit, and displaying, in a case where the radiographic image does not meet the pre-determined standard, a high-resolution image on the display unit,
wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

18. A non-transitory computer-readable storage medium storing a program for causing a computer to execute a method, the method comprising:
receiving a plurality of reduced images included in a radiographic image in stages from a radiographic imaging apparatus; and
displaying, in a case where the radiographic image meets a pre-determined standard, a first image generated from reduced images included in the plurality of reduced images on a display unit, and displaying, in a case where the radiographic image does not meet the pre-determined standard, on the display unit a second image generated from reduced images which are included in the plurality of reduced images and of which the number is larger than the number of the reduced images from which the first image is generated,
wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

19. A non-transitory computer-readable storage medium storing a program for causing a computer to execute a method, the method comprising:
receiving a radiographic image from a radiographic imaging apparatus; and
displaying, in a case where the radiographic image meets a pre-determined standard, a low-resolution image on a display unit, and displaying, in a case where the radiographic image does not meet the pre-determined standard, a high-resolution image on the display unit,
wherein the pre-determined standard is not met when at least one of following conditions is satisfied: (a) a body movement is detected from the radiographic image, (b) a particular part in the radiographic image is missing, and (c) an amount of emitted radiation detected from the radiographic image exceeds a pre-set threshold.

* * * * *